(12) United States Patent
Moore et al.

(10) Patent No.: US 7,998,938 B2
(45) Date of Patent: Aug. 16, 2011

(54) CANCER TREATMENT BY COMBINED INHIBITION OF PROTEASOME AND TELOMERASE ACTIVITIES

(75) Inventors: Malcolm A.S. Moore, New York, NY (US); Allison C. Chin, Stanford, CA (US)

(73) Assignees: Geron Corporation, Menlo Park, CA (US); Memorial Sloan-Kettering Cancer Center, New York, NY (US)

( * ) Notice: Subject to any disclaimer, the term of this patent is extended or adjusted under 35 U.S.C. 154(b) by 467 days.

(21) Appl. No.: 11/918,581

(22) PCT Filed: Apr. 14, 2006

(86) PCT No.: PCT/US2006/014137
§ 371 (c)(1),
(2), (4) Date: Feb. 7, 2008

(87) PCT Pub. No.: WO2006/113470
PCT Pub. Date: Oct. 26, 2006

(65) Prior Publication Data
US 2010/0010064 A1  Jan. 14, 2010

Related U.S. Application Data

(60) Provisional application No. 60/671,630, filed on Apr. 15, 2005.

(51) Int. Cl.
*A16K 48/00* (2006.01)
(52) U.S. Cl. .......... 514/44; 536/24.5; 435/325; 435/375
(58) Field of Classification Search .................. None
See application file for complete search history.

(56) References Cited

U.S. PATENT DOCUMENTS

| | | | |
|---|---|---|---|
| 5,760,062 A | 6/1998 | Gaeta et al. | |
| 6,331,399 B1 | 12/2001 | Monia et al. | |
| 6,444,650 B1 | 9/2002 | Cech et al. | |
| 6,548,298 B2 | 4/2003 | Villeponteau et al. | |
| 2005/0113325 A1* | 5/2005 | Gryaznov et al. | 514/44 |

FOREIGN PATENT DOCUMENTS

WO  WO2005/023994 A2  3/2005

OTHER PUBLICATIONS

Akiyama et al. Effects of Oligonucleotide N3-N5 Thiophosphoramidate (GRN163) Targeting Telomerase RNA in Human Multiple Myeloma Cells. Cancer Research 63: 2003, 6187-6194.*
Chen et al. Consequences of Telomerase Inhibition and Combination Treatments for the Proliferation of Cancer Cells. Cancer Research 63, 2003: 5917-5925.*
LeBlanc et al. Proteosome Inhibitor PS341 inhibits human myeloma cell growth in vivo and prolongs survival in a murine model. Cancer Research 62, 2002: 4996-5000.*
Polushin et al. Antisense pro-drugs: 5'-ester oligodeoxynucleotides. Nucleic Acids Research 1994: 5492-5496.*
Pongracz et al. Oligonucleotide N3'-P5' thiphosphoroamidates: synthesis and properties. Tetrahedron Letters 40 1999: 7661-7664.*
Adams, J., *Trends Mol. Med.*, 8(4 Suppl):S49-S54 (2002).
Asai et al., *Cancer Research* 63:3931-3939 (2003).
Blackburn, *Ann. Rev. Biochem.*, 61:113-129 (1992).
Bogyo et al., *Proc. Natl. Acad. Sci. USA*, 94:6629-6634 (1997).
The International Search Report and Written Opinion for PCT application PCT/US2006/014137 dated Sep. 27, 2006.
Dikmen et al. *Cancer Res.*, 65(17):7866-73 (2005).
Elofsson, et al., *Chem Biol*, 6(11):811-822 (1999).
Emanuele et al., *Int J Oncol.*, 21:857-865 (2002).
Fanucchi MP et al., *J. of Clinical Oncology*, 23:629s (Abstract 7034) (2005).
Gowan et al., *Molecular Pharmacology*, 61:1154-1162 (2002).
Gryaznov et al., *Nucleosides Nucleotides Nucleic Acids* 22(5-8):577-81 (2003).
Hanada et al., *J Antibiot*, 45(11):1746-1752 (1992).
Harley, *Mutation Research*, 256:271-282 (1991).
Herbert, B.S. et al., *Oncogene*, 24(33):5262-5268 (2005).
Kamat et al., *Molecular Cancer Therapeutics*, 3(3):279-290 (2004).
Koguchi et al., *The Journal of Antibiotics*, 52(12):1069-1076 (1999).
Koguchi et al., *The Journal of Antibiotics*, 53(2):105-109 (2000).
Pruzan et al., *Nucl. Acids Research*, 30:559-568 (2002).
Rock et al., *Cell*, 78:761-771 (1994).
Shea-Herbert et al., *Oncogene*, 21:638-642 (2002).
Sun et al., Cancer Letters, 232(2):161-169 (2006).
Ward & Autexier, *Molecular Pharmacology*, 68:779-786 (2005).
Ward et al., *The Journal of Biological Chemistry*, 274(7):4309-4318 (1999).
Wilk and Orlowski, *Journal of Neurochemistry*, 40:842-849 (1983).
Wu et al., Circulation, 109(13):1660-1667 (2004).
Written Opinion and Extended European Search Report mailed Aug. 4, 2010 for related EP Patent Application No. EP 06750227.8.

* cited by examiner

*Primary Examiner* — Kimberly Chong
(74) *Attorney, Agent, or Firm* — King & Spalding LLP; Peter J. Dehlinger; LeeAnn Gorthey

(57) ABSTRACT

A method and kit for inhibiting the proliferation of cancer cells are disclosed, based on a combination of a proteasome inhibitor and a telomerase inhibitor. When used in cancer therapy, the two compounds in combination enhance the anticancer treatment efficacy obtained with the proteasome inhibitor alone or the telomerase inhibitor alone. Preferably, efficacy is supraadditive or synergistic in nature relative to the combined effects of the individual agents, with minimal exacerbation of side effects.

16 Claims, 5 Drawing Sheets

CANCER TREATMENT BY COMBINED INHIBITION OF PROTEASOME AND TELOMERASE ACTIVITIES

This application is a 35 USC §371 application of International Application No. PCT/US2006/014137 filed Apr. 14, 2006, designating the United States, which claims priority to U.S. Application No. 60/671,630 filed Apr. 15, 2005, now abandoned, all of which are hereby incorporated by reference in their entirety.

FIELD OF THE INVENTION

The invention is directed to anticancer treatment, and in particular to inhibition of tumor growth or cancer-cell proliferation, by treatment with a telomerase inhibitor in combination with a proteasome inhibitor.

BACKGROUND

Although many cancers can be cured by surgical resection, chemotherapy is often used as an adjunct to surgical therapy, and it is widely used in the treatment of inoperable or metastatic malignancy. In view of the continuing high number of deaths each year resulting from cancer, a continuing need exists to identify effective and relatively nontoxic therapeutic regimens for use in anticancer treatment.

Many effective chemotherapeutic agents have been identified over the past few decades, and these are generally grouped into several categories on the basis of their mechanism of action. Combined-therapy treatments have become more common, in view of the perceived advantage of attacking the disease via multiple avenues. In practice, however, many such combinations do not provide even simple additivity of therapeutic effects.

Ideally, a combined-drug approach for cancer treatment should provide a significant boost in efficacy, and/or a significant reduction in undesired side effects, due to a reduced dose of the more toxic component, and/or a reduction in the development of drug-resistance in the cancer being treated. Particularly desirable are combination therapies which produce therapeutic results that are supraadditive or synergistic in nature relative to the effects of the individual agents, with minimal exacerbation of side effects.

SUMMARY

The invention includes a method for inhibiting the proliferation of cancer cells, by (a) exposing the cells to a proteasome inhibitor of the type effective to inhibit the chymotrypsin-like activity of proteasomes, and (b) either proceeding, following, or concomitantly with step (a), exposing the cells to a telomerase inhibitor. In one embodiment, the amount of proteasome inhibitor to which the cells are exposed is effective, by itself, to inhibit proliferation of the cancer cells. In a further embodiment, the amount of each inhibitor is effective, by itself, to inhibit proliferation of the cancer cells. Preferably, the combination provides a enhanced inhibiting effect relative to either component alone; more preferably, the combination provides a supraadditive or synergistic effect relative to the combined or additive effects of the components.

The telomerase inhibitor may include an oligonucleotide having nuclease-resistant intersubunit linkages and an oligonucleotide sequence effective to bind by sequence-specific hybridization to a template region of hTR. The internucleoside linkages in the oligonucleotide may be selected from N3'→P5' phosphoramidate and N3'→P5' thiophosphoramidate linkages. The telomerase inhibitor may include a lipid moiety, such as a fatty acid, sterol, or derivative thereof, which is attached covalently at one end of the oligonucleotide. The oligonucleotide may be 10-20 bases in length, preferably 13-20 bases in length, and may have the sequence identified by SEQ ID NO:12 (5'-TAGGGTTAGACAA-3'). One exemplary telomerase inhibitor is the compound designated herein as GRN163L.

The proteasome inhibitor may be (a) a synthetic peptide boronate, such as bortezomib (also known as Velcade™ and PS341), (b) a synthetic peptide aldehyde, such as MG132, MG115, PSI, or ALLN, (c) a synthetic sulfone tripeptide, (d) a synthetic epoxoketone, such as epoxomicin, or (e) a microbial chymotrypsin-like inhibitor, such as lactacystin. One preferred proteasome inhibitor is bortezomib.

The method may be used for use in treating a subject having a cancer, where, preferably, exposing step (a) includes administering the proteasome inhibitor to the subject in an amount effective, when administered alone, to inhibit proliferation of cancer cells in the subject. In a further embodiment, each exposing step (a) and (b) includes administering the respective inhibitor to the subject in an amount effective, when administered alone, to inhibit proliferation of cancer cells in the subject.

The method may be used in treating a variety of cancers in a subject. In exemplary embodiments, the method is used in treating multiple myeloma, non-small-cell lung carcinoma, or prostate cancer in a subject. Where the telomerase inhibitor is the compound GRN163L, it may be administered to the subject by intravenous infusion, under infusion conditions effective to produce a blood concentration of the inhibitor of between 1 nM and 100 uM.

In another aspect, the invention is directed to a method for enhancing the anti-cancer treatment efficacy of the proteasome inhibitor bortezomib in a subject. The method includes administering to the subject, before, during, or after administering bortezomib, an oligonucleotide telomerase inhibitor of the type composed of an oligonucleotide having nuclease-resistant intersubunit linkages and an oligonucleotide sequence effective to bind by sequence-specific hybridization to a template region of hTR. Preferably, the amount of the telomerase inhibitor is effective to inhibit the proliferation of cancer cells in the subject when the telomerase inhibitor is administered alone.

The two inhibitors may be administered to the subject as a composition containing both inhibitors. The enhancement of treatment efficacy may be evidenced, for example, by an increased survival time of the subject, or by an inhibition of tumor growth in the subject, relative to treatment with bortezomib alone. The method may be used in treating a variety of cancers in a subject. In exemplary embodiments, the method is used in treating multiple myeloma, non-small-cell lung carcinoma, or prostate cancer in a subject.

The oligonucleotide may be 10-20 bases in length. Preferably, the oligonucleotide is 13-20 bases in length and includes the sequence identified by SEQ ID NO: 12 (5'-TAGGGTTA-GACAA-3'). An exemplary telomerase inhibitor is the compound identified as GRN163L, or an analog thereof. This compound has (i) N3'→P5' thiophosphoramidate internucleoside linkages; (ii) the sequence identified as SEQ ID NO:12; and (iii) a palmitoyl (C16) moiety linked to the 5' end of the oligonucleotide through a glycerol or aminoglycerol linker.

The invention may also be practiced to identify cancer patients who are candidates for effective anti-cancer treatment with a telomerase inhibitor. The candidate patients are those whose cancer is responding to treatment with bortezomib, or a related proteasome inhibitor, but for whom combined treatment with a telomerase inhibitor is desired to enhance the anti-tumor efficacy of the proteasome inhibitor alone.

Also disclosed in a kit for use in cancer therapy, comprising (a) a dose of a proteasome inhibitor of the type capable of inhibiting the chymotrypsin-like site of proteasomes, in an amount of the inhibitor effective, when administered alone, to inhibit the proliferation of cancer cells in the subject, and (b) a dose of an oligonucleotide telomerase inhibitor having nuclease-resistant intersubunit linkages, and an oligonucleotide sequence effective to bind by sequence-specific hybridization to a template region of hTR. In one embodiment, the telomerase inhibitor is provided in an amount effective, when administered alone, to inhibit proliferation of cancer cells in the subject.

In an exemplary embodiment, the proteasome inhibitor is bortezomib and the telomerase inhibitor is the compound identified as GRN163L, or an analog thereof. The latter compound has (i) N3'→P5' thiophosphoramidate internucleoside linkages in the oligonucleotide; (ii) the sequence identified as SEQ ID NO: 12; and (iii) a palmitoyl (C16) moiety linked to the 5' end of the oligonucleotide through a glycerol or aminoglycerol linker.

Also provided is a kit comprising a telomerase inhibitor and bortezomib, for use in therapy, such as the treatment of cancer. Such therapy preferably comprises administering bortezomib to a subject, either preceding, following, or concomitantly with administration of said telomerase inhibitor. The telomerase inhibitor is preferably a nuclease-resistant oligonucleotide which binds in a sequence-specific manner to the template region of hTR. Preferred and/or exemplary inhibitors and cancer indications are as set out above.

In a related aspect, the invention provides a kit containing a dose of an oligonucleotide telomerase inhibitor having nuclease-resistant intersubunit linkages and an oligonucleotide sequence effective to bind by sequence-specific hybridization to a template region of hTR, preferably in an amount effective to inhibit proliferation of cancer cells in a subject. The kit preferably includes an insert with instructions for administration; such an insert may provide a user with one set of instructions for using the inhibitor in monotherapy and a separate set of instructions for using the inhibitor in combination with bortezomib or other proteasome inhibitor. The set of instructions for the combination therapy may recommend (i) a lower dose of the telomerase inhibitor, when used in combination with the proteasome inhibitor, (ii) a lower dose of the proteasome inhibitor, when used in combination with the proteasome inhibitor, and/or (iii) a different dosing regimen for one of both inhibitors than would normally be recommended.

Also provided is the use of a telomerase inhibitor for preparation of a medicament for use in treatment of cancer, wherein said treatment comprises administering said telomerase inhibitor to a subject in combination with bortezomib. Said treatment may comprise administering bortezomib to the subject either preceding, following, or concomitantly with the telomerase inhibitor, which is preferably a nuclease-resistant oligonucleotide which binds in a sequence-specific manner to the template region of hTR.

In a related aspect, the invention provides the use of a proteasome inhibitor and a telomerase inhibitor, in the manufacture of a medicament for treating cancer in a subject. Preferred and/or exemplary inhibitors and cancer indications are as set out above.

Further disclosed is the use of a telomerase inhibitor in the manufacture of a medicament for treating cancer in a subject who is being treated with a proteasome inhibitor, for purposes of enhancing the anti-cancer efficacy of a proteasome inhibitor in the subject. Preferred and/or exemplary inhibitors and cancer indications are as set out above.

These and other objects and features of the invention will become more fully apparent when the following detailed description of the invention is read in conjunction with the accompanying drawings.

DETAILED DESCRIPTION OF THE INVENTION

I. Definitions

Figure 1:
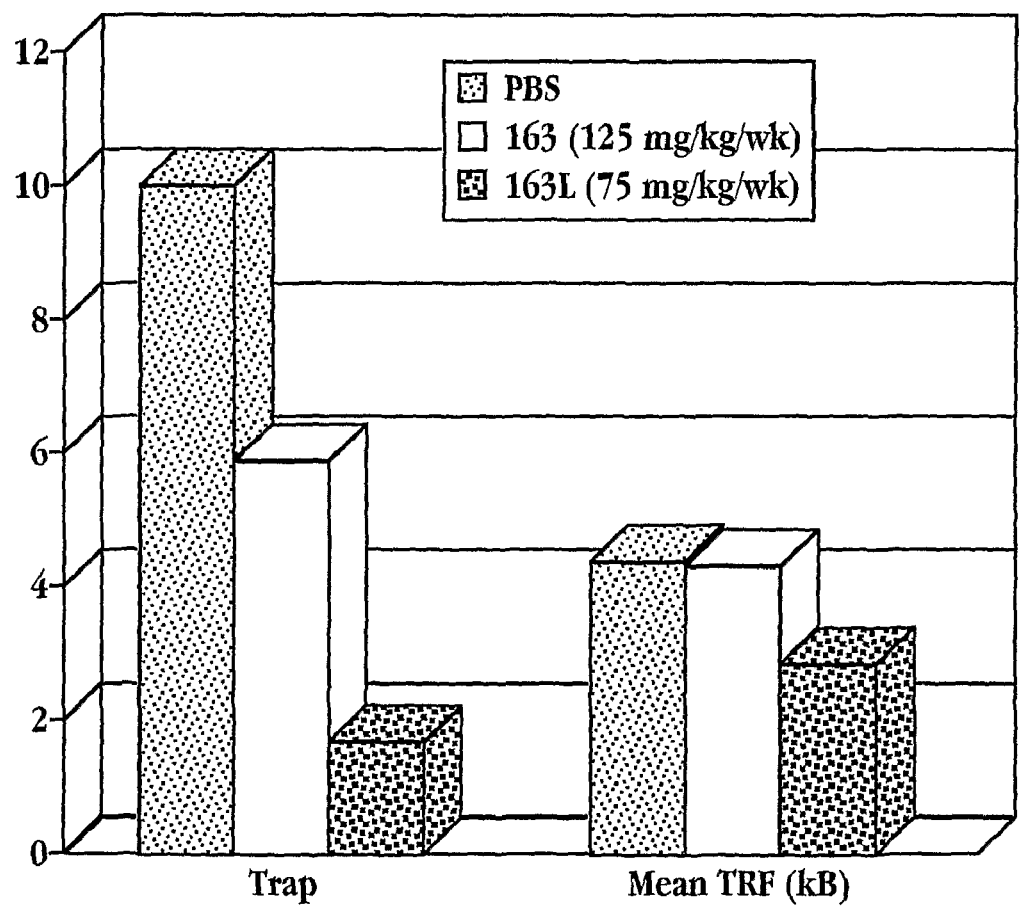
FIGS. 1-2 show enhancement of telomerase inhibiting activity of an NPS oligonucleotide hTR template inhibitor (GRN163) by conjugation to a lipid (to produce GRN163L), in human myeloma tumor xenografts (FIG. 1) and liver cells (FIG. 2), respectively, in mice.

The terms below have the following meanings unless indicated otherwise.

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'→P5' thiophosphoramidate, and phosphorothioate linkages. The term also includes such polymers or oligomers having modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

The term "nucleoside" includes the natural nucleosides, including 2'-deoxy and 2'-hydroxyl forms, e.g., as described in Kornberg and Baker, DNA Replication, 2nd Ed. (Freeman, San Francisco, 1992), and analogs. "Analogs", in reference to nucleosides, includes synthetic nucleosides having modified nucleobase moieties (see definition of "nucleobase" below) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews* 90:543-584, 1990). An oligonucleotide containing such nucleosides, and which typically contains synthetic nuclease-resistant internucleoside linkages, may itself be referred to as an "analog".

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. Preferred lipids are fatty acids and their derivatives, hydrocarbons and their derivatives, and sterols, such as cholesterol.

Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters.

The term "hydrocarbon" encompasses compounds that consist only of hydrogen and carbon, joined by covalent bonds. The term encompasses open chain (aliphatic) hydrocarbons, including straight chain and branched hydrocarbons, and saturated as well as mono- and poly-unsaturated hydrocarbons. The term also encompasses hydrocarbons containing one or more aromatic rings.

As used herein, the term "lipid" also includes amphipathic compounds containing both lipid and hydrophilic moieties.

The term "substituted" refers to a compound which has been modified by the exchange of one atom or moiety for another, typically substitution of hydrogen by a different atom or moiety. In particular, the term is used in reference to halogenated hydrocarbons and fatty acids, particularly those in which one or more hydrogen atoms are substituted with fluorine.

An "hTR template inhibitor" is a compound that blocks the template region (the region spanning nucleotides 30-67 of SEQ ID NO: 1 herein) of the RNA component of human telomerase, thereby inhibiting the activity of the enzyme. The inhibitor is typically an oligonucleotide that is able to hybridize to this region. Preferably, the oligonucleotide includes a sequence effective to hybridize to a more specific portion of this region, having sequence 5'-CUAACCCUAAC-3' (SEQ ID NO: 2), spanning nucleotides 46-56 of SEQ ID NO: 1 herein.

A compound is said to "inhibit the proliferation of cancer cells" if the proliferation of cells in the presence of the compound is less than that observed in the absence of the compound. That is, proliferation of the cells is either slowed or halted in the presence of the compound. Inhibition of cancer-cell proliferation may be evidenced, for example, by reduction in the number of cells or rate of expansion of cells, reduction in tumor mass or the rate of tumor growth, or increase in survival rate of a subject being treated.

Administration of a telomerase inhibitor to a subject is effective to "enhance the anti-cancer treatment efficacy of a proteasome inhibitor," if the subject shows a reduced rate of tumor growth and/or an enhanced survival rate with combined therapy over therapy with the proteasome inhibitor alone.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

II. Treatment of Cancer with Proteasome Inhibitors

Proteasomes control the half-life of many short-lived regulatory proteins, such as those involved in the cell cycle. The ubiquitin-proteasome pathway plays an essential role in regulating the intracellular concentration of specific proteins, thereby maintaining homeostasis within cells. Inhibition of the 26S proteasome prevents this targeted proteolysis, which can affect multiple signaling cascades within the cell. This disruption of normal homeostatic mechanisms can lead to cell cycle arrest and cell death. Tumor cells are more susceptible to these effects than normal cells, in part because they divide more rapidly and in part because many of their normal regulatory pathways are disrupted.

Several compounds that inhibit one of more of the proteolytic activities of proteasomes have been developed for use in cancer treatment. One general class of proteasome inhibitors is those that inhibit the chymotrypsin-like activity of proteasomes. These compounds specifically interact with a key threonine within the digestive site (catalytic site) of the proteasome, and their inhibitory activity can be assayed, for example, by the ability of the compound to block the proteolytic conversion of known proteasome substrates for chymotrypsin-like activity. Such substrates are supplied, for example, by BIOMOL International LP, as can be accessed via the Online Catalog at the BIOMOL website, under the category "Proteasome Substrates for Chymotrypsin-like Activity". This inhibitory activity may not be exclusive, and some compounds known to inhibit the chymotrypsin-like activity of proteasomes also act to inhibit other proteasome activities, such as the trypsin-like and peptidyl-glutamyl peptide hydrolyzing (PGPH) activities of proteasomes.

Several classes of proteasome inhibitors that inhibit the chymotrypsin-like activity of proteasomes are known. One important class includes the peptidyl boronates, such as bortezomib, also known as Velcade™ or PS341, a modified dipeptidyl boronic acid modified dipeptide boronic acid having the chemical name [(1R)-3-methyl-1-[[(2S)-1-oxo-3-phenyl-2-[(pyrazinylcarbonyl)amino)]propyl]amino]butyl] boronic acid, and produced by Millenium Pharmaceuticals.

Bortezomib is the first proteasome inhibitor to enter clinical trials for treatment of cancer, and the compound has been clinically approved and indicated for treatment of multiple myeloma. In addition, a phase II randomized trial has determined that bortezomib has significant activity as a single agent with non-small cell lung cancer (NSCLC) (Fanucchi M P et al., *J. Clinical Oncology* 2005; 23:629). Other clinical investigations have pointed to antitumor effects of bortezomib in breast, colon, neuroendocrine, and renal cancers, as well as in melanoma, sarcoma, chronic myelogenoius leukemia, and non-Hodgkin's lymphoma. Encouraging activity has also been reported in patients with aggressive forms of lymphoma such as mantle cell lymphoma. Typical drug dose in cancer treatment is about 1-2 mg/m$^2$.

Several other proteasome inhibitors function, at least in part, by the same mechanism of inhibiting the chymotrypsin-like activity of proteasomes, and are also suitable for use in the combination cancer treatment of the invention. These include:

(a) synthetic peptide aldehydes which reversibly inhibit the chymotrypsin-like activity, such as MG132, which has been found to induce apoptosis in human hepatoblastoma HepG2 cells (Emanuele et al., *Int J Oncol.,* 21:857-865, 2002); MG115, which has been shown to induce apoptosis in Rat-1 and PC12 cells (Saito et al., *Neurosci Lett,* 89:102-107, 1990 and Rock et al., *Cell,* 78:761-771, 1994); ritonavir, an inhibitor of HIV-I protease that inhibits the chymotryptic activity of mouse and human proteasomes (Schmidtke et al., *J Biol Chem,* 274(50):35734-35740, 1999), ALLN, which has been shown to induce apoptosis in insulinoma cells; the proteasome inhibitors I, II, III and IV (PSI, PSII, PSIII, boronic acid based, and PSIV), where PSI has been shown to induce apoptosis in human mesothelioma cells (Sun et al., *Cancer Lett,* 232(2):161-169, 2006) and to prevent the expression of plasminogen activator and inhibit blood vessel formation in embryonic chick chorioallantoic membrane (Oikawa et al., *Biochem Biophys Res Commun,* 246:243-248, 1998); Z-GGL (Wilk and Orlowski, *J Neurochem,* 40:842-849, 1983); Z-IIF-H; Z-LLY-COCHO; and peptide glyoxals where an additional ketone moiety is added at the a position of the peptide aldehydes (Lynas et al., *Bioorg Med Chem Lett,* 8:373-378, 1998), (b) synthetic sulfone tripeptides, such as carboxybenzyl-leucyl-leucyl-leucine vinyl sulfone (Z-L$_3$VS) and related derivatives such as NIP-L$_3$VS (a nitrophenol derivative) both of which have been shown to irreversibly inhibit proteasome activity in vivo (Bogyo et al., *PNAS USA,* 94:6629-6634, 1997); and NLVS, an irreversible inhibitor of chymotrypsin-like activity, (c) synthetic epoxyketones, such as YU 101 (Ac-hFLFL-epoxide), a potent antiproliferative and anti-inflammatory agent (Elofsson, et al., *Chem Biol,* 6(11):811-822, 1999) that is structurally related to epoxomicin, and (d) microbial chymotrypsin-like inhibitors, such as lactacystin and derivatives, which is a microbial metabolite isolated from *Streptomyces* that has been found to inhibit the formation of vascular endothelial tubes in vitro and prevent the expression of plasminogen activator and inhibit blood vessel formation in embryonic chick chorioallantoic membrane (Oikawa et al., *Biochem Biophys Res Commun,* 246: 243-248, 1998); epoxoketones, such as epoxomycin, which exhibits in vivo antitumor activity against B16 melanoma (Hanada et al., *J Antibiot,* 45(11):1746-1752, 1992) as well as in vivo anti-inflammatory activity (Meng, et al., *PNAS USA,* 96:10403-10408, 1999), eponemycin, which is an antibiotic that has anti-angiogenic activity (Oikawa et al., *Biochem Biophys Res Commun,* 181(3):1070-1076, 1991), and its derivative dihydroeponemycin; aclarubicin (aclacinomycin), an anthracycline antibiotic produced by *Streptomyces galilaeus* having potent antineoplastic activity, especially in the treatment of leukemias; tyropeptin A and B, which are isolated from the culture broth of *Kitasatospora* sp.; gliotoxin, an immunomodulatory fungal toxin that has been shown to induce apoptosis in a variety of cells (Ward et al., *J. Biol. Chem.,* 274:4309, 1999); TMC-86A and B, which were isolated from *Streptomyces* sp. fermentation broth (Koguchi et al., *J Antibiot,* 52(12):1069-1076, 1999); TMC-95 isolated from *Apiospora monagnei* (Koguchi et al., *J Antibiot,* 53(2): 105-109, 2000); TMC-96, which was isolated from *Saccharothrix* sp. fermentation broth (Koguchi et al., 1999); and PR39, a proline-arginine-rich peptide antibiotic that was originally isolated from pig intestine (PR11 is a derivative of PR39 and FALL-39 is the tentative human counterpart) has been shown to inhibit chymotrypsin-like activity when studied with fluorogenic peptide substrates and recent studies have shown that PR39 stimulates angiogenesis and inhibits inflammatory responses (Li et al., Nature Medicine, 6(1):49-55, 2000) and has been found to inhibit apoptosis in hypoxic endothelial cells (Wu et al., *Circulation,* 109(13):1660-1667, 2004).

III. Treatment of Cancer with a Telomerase Inhibitor

Telomerase is a ribonucleoprotein that catalyzes the addition of telomeric repeat sequences (having the sequence 5'-TTAGGG-3' in humans) to chromosome ends. See e.g. Blackburn, 1992, *Ann. Rev. Biochem.* 61:113-129. The enzyme is expressed in most cancer cells but not in mature somatic cells. Loss of telomeric DNA may play a role in triggering cellular senescence; see Harley, 1991, *Mutation Research* 256:271-282. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides, preferably oligonucleotides having nuclease resistant linkages, as well as small molecule compounds.

A. Small Molecule Compounds

Small molecule inhibitors of telomerase include, for example, BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin. These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277(18):15566-72, 2002); AZT and other nucleoside analogs, such as ddG and ara-G (see, for example, U.S. Pat. Nos. 5,695,932 and 6,368, 789), and certain thiopyridine, benzo[b]thiophene, and pyrido[b]thiophene derivatives, described by Gaeta et al. in U.S. Pat. Nos. 5,767,278, 5,770,613, 5,863,936, 5,656,638 and 5,760,062. One example is 3-chlorobenzo[b]thiophene-2-carboxy-2'-[(2,5-dichlorophenyl amino)thia]hydrazine, described in U.S. Pat. No. 5,760,062.

B. Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR).

The nucleotide sequence of the RNA component of human telomerase (hTR) is shown in the Sequence Listing below (SEQ ID NO: 1), in the 5'→3' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The template sequence of the RNA component is located within the region defined by nucleotides 46-56 (5'-CUAACCCUAAC-3'), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100: 503-514, 2000; Kim et al., *Proc. Natl. Acad. Sci. USA* 98 (14):7982-7987, 2001). The design of antisense, ribozyme or small interfering RNA (siRNA) agents to inhibit or cause the destruction of mRNAs is well known (see, for example, Lebedeva, I, et al. Annual Review of Pharmacology and Toxicology, Vol. 41: 403-419, April 2001; Macejak, D, et al., Journal of Virology, Vol. 73 (9): 7745-7751, September 1999, and Zeng, Y. et al., PNAS Vol. 100 (17) p. 9779-9784, Aug. 19, 2003) and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function. See, for example, Villeponteau et al., U.S. Pat. No. 6,548,298.

A preferred target region of hTR is the template region, spanning nucleotides 30-67 of SEQ ID NO:1. Oligonucleotides targeting this region are referred to herein as "hTR template inhibitors" (see e.g. Herbert et al., *Oncogene* 21 (4):638-42 (2002).) Preferably, such an oligonucleotide includes a sequence which is complementary or near-complementary to some portion of the 11-nucleotide region having sequence 5'-CUAACCCUAAC-3', spanning nucleotides 46-56 of SEQ ID NO: 12.

Another preferred target region is the region spanning nucleotides 137-179 of hTR (see Pruzan et al., *Nucl. Acids Research*, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the following:

| hTR Targeting Sequence | Region of SEQ ID NO: 1 | SEQ ID NO: |
|---|---|---|
| ACATTTTTGTTTGCTCTAG | 160-179 | 2 |
| GCTCTAGAATGAACGGTGGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGGC | 143-155 | 10 |
| ATGAACGGTGGAAGGCGG | 144-158 | 11 |
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | 19 |
| CAGTTAGGG | 50-58 | 20 |
| CCCTTCTCAGTT | 54-65 | 21 |
| CGCCCTTCTCAG | 56-67 | 22 |

The internucleoside linkages in the oligonucleotide may include any of the available oligonucleotide chemistries, e.g. phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In preferred embodiments, the oligonucleotide has at least one N3'→P5' phosphoramidate (NP) or N3'→P5' thiophosphoramidate (NPS) linkage, which linkage may be represented by the structure: 3'-(-NH—P(=O)(—XR)—O-)-5', wherein X is O or S and R is selected from the group consisting of hydrogen, alkyl, and aryl; and pharmaceutically acceptable salts thereof, when XR is OH or SH. More preferably, the oligonucleotide includes all NP or, most preferably, all NPS linkages.

A particularly preferred sequence for an hTR template inhibitor oligonucleotide is the sequence complementary to nucleotides 42-54 of SEQ ID NO: 12 above. The oligonucleotide having this sequence (TAGGGTTAGACA) and N3'→P5' thiophosphoramidate (NPS) linkages is designated herein as GRN163. See, for example, Asai et al., *Cancer Research* 63:3931-3939 (2003); Gryaznov et al., *Nucleosides Nucleotides Nucleic Acids* 22(5-8):577-81 (2003).

As shown in Table 1 below, this oligonucleotide (first row of table) inhibits telomerase at low concentrations in a biochemical assay (FlashPlate™; see Experimental Section). An alternative 13-mer, having the sequence CAGTTAGGGTTAG, complementary to nucleotides 46-58 of SEQ ID NO: 1 (fifth row of table), showed near-equivalent activity in the FlashPlate™ assay. The corresponding NP-linked oligonucleotide, and shorter (11- and 12-mer) oligonucleotides targeting the same region (complementary to nucleotides 42-53 and 42-42, respectively, of SEQ ID NO: 1), showed moderate activity. The effect is clearly sequence-specific, as shown by the mismatch and non-targeting sequences in the table.

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell.

TABLE 1

Inhibition of Telomerase by NPS Oligonucleotides: Biochemical (FlashPlate) Assay

| Sequence, 5' to 3' | Description | $IC_{50}$, nM |
|---|---|---|
| TAGGGTTAGACAA SEQ ID NO: 12 | 13-mer (GRN163) | 0.045 ± 0.007 |
| TAGGTGTAAGCAA (SEQ ID NO: 23) | Mismatch of GRN163 sequence | 80 ± 31 |
| TTGTCTAACCCTA (SEQ ID NO: 24) | Complement of GRN163 sequence | 1000 ± 46 |
| TAGGGTTAGACAA ATCCCAATCTGTT | Duplex of GRN163 sequence | 8.9 ± 3.0 |
| CAGTTAGGGTTAG (SEQ ID NO: 13) | Alternative targeting 13-mer | 0.049 ± 0.007 |
| TAGGGTTAGACA (SEQ ID NO: 14) | 12-mer; truncation of GRN163 sequence | 0.36 ± 0.2 |
| TAGGGTTAGAC (SEQ ID NO: 15) | 11-mer; truncation of GRN163 sequence | 0.85 ± 0.35 |
| GTTAGGGTTAG (SEQ ID NO: 16) | Alternative targeting 11-mer | 0.51 ± 0.13 |
| GTTGAGTGTAG (SEQ ID NO: 25) | Mismatch of alternative targeting 11-mer | 177 ± 93 |
| TAGGGTTAGACAA (SEQ ID NO: 12) | 13-mer (GRN163 sequence) with NP backbone | 0.7 ± 0.1 |
| TAGGTGTAAGCAA (SEQ ID NO: 2) | Mismatch of GRN163 sequence with NP backbone | >1000 |
| TTAGGG (SEQ ID NO: 26) | Telomere repeat unit | >1000 |
| TTTTTTTTTT (SEQ ID NO: 27) | Oligo-T 10-mer | >1000 |

C. Lipid-Oligonucleotide Conjugates

Preferably, the oligonucleotide-based enzyme inhibitor includes at least one covalently linked lipid group (see US Pubn. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadecanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below.

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown below) is designated GRN163L herein. In a second exemplary structure, the lipid, as a palmitoyl amide, is conjugated through the terminal 3' amino group of an NPS oligonucleotide.

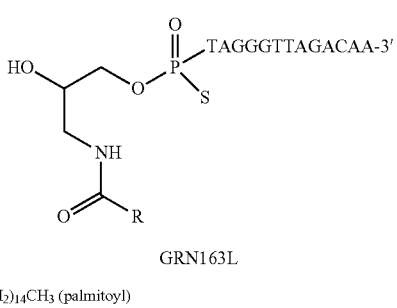

GRN163L

R = ——(CH$_2$)$_{14}$CH$_3$ (palmitoyl)

As shown in Table 2, conjugation of a single fatty acid-type lipid significantly increased telomerase inhibitory activity in cell systems relative to the unconjugated oligonucleotide.

TABLE 2

Inhibition of Telomerase by Lipid-Conjugated NPS Oligonucleotides (based on GRN163)

| Lipid Substitution | Tm (° C.) of duplex with RNA | IC$_{50}$ in vitro, HT-3 cells, nM |
|---|---|---|
| none (GRN163) | 70.0 | 1600 |
| 3'-palmitic (GRN163L) | 66.5 | 160 |
| 3'-stearic | 67.1 | 140 |
| 3'-(bis)stearic | ~40 | 1960 |
| 3'-oleic | 66.8 | 930 |
| NH—C$_{16}$ (palmitoyl) on 3$^{rd}$ 5' residue (G) | 62.6 | 500 |
| 5'-palmitic | 65.5 | 112 |
| 3'-palmitic-5'-palmitic | 61.3 | ~10000 |
| 3'-trityl | 66.1 | 3000 |

The effect of lipid conjugation on pharmacokinetics is illustrated by the data shown in Table 3, below, for a 4 mg/kg dose administered in rats. Target organ concentrations 6 hours after administration were also more favorable for GRN163L, with approx. 4-5 μM found in liver, kidney, and fat tissue, 2-3 μM in bone marrow and spleen, and about 0.5 μM in lymph node. Distribution of the unlipidated oligonucleotide, GRN163, was primarily to the kidney (about 18 μM), with only 1 μM or less in the remaining organ tissues noted above.

Table 4 presents further data directed to telomerase inhibition in vitro by GRN163 (unconjugated) and GRN163L (lipidated) in various cancer cell lines.

TABLE 3

Comparative Pharmacokinetics of Lipidated (GRN163L) and Unlipidated (GRN163) NPS Oligonucleotide (Rat, 4 mg/kg dose)

| | GRN163 | GRN163L |
|---|---|---|
| T$_{1/2}$α, min | 17 | 20 |
| T$_{1/2}$β, hrs | 65-86 | 68-72 |
| AUC$_{0-\infty}$, μg-hr/g | 27 | 120 |
| C$_{MAX}$, μg/ml | 16 | 58 |
| % excreted in 24 h | 45 | 13 |

TABLE 4

Comparative Telomerase Inhibitory Activity of Lipidated (GRN163L) and Unlipidated (GRN163) NPS Oligonucleotide in vitro

| Cell Line | GRN163 IC$_{50}$ (μM) | GRN163L IC$_{50}$ (μM) |
|---|---|---|
| HT-3 (Cervical) | 1.62 | 0.3 |
| U251 (Glioblastoma) | 1.75 | 0.17 |
| U87 (Glioblastoma) | 0.75 | 0.11 |
| Hep3B (Hepatoma) | 6.5 | 0.36 |
| HepG2 (Hepatoma) | 2.72 | 0.48 |
| NCI-H522 (Lung) | 2.59 | 0.23 |
| RPMI 8226 (Myeloma) | 2.67 | 0.38 |
| Ovcar5 (Ovarian) | 3.74 | 0.92 |
| DU 145 (Prostate) | 1.4 | 0.15 |

Figure 2:
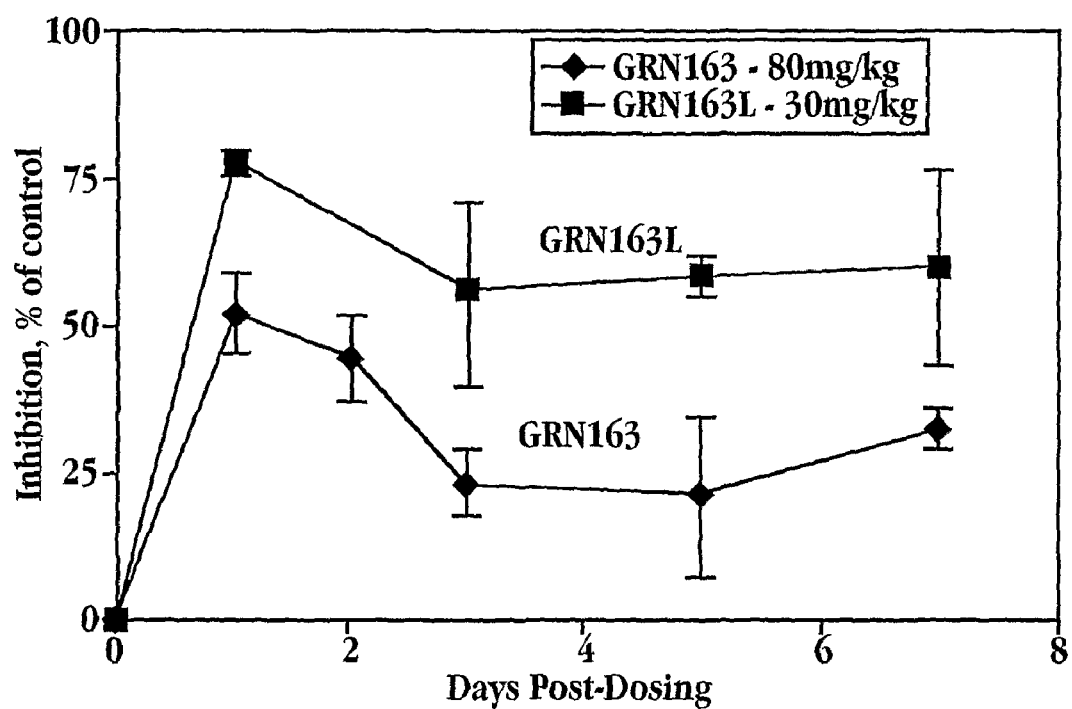

The conjugated oligonucleotide GRN163L had significantly greater telomerase inhibiting activity in vivo than the unconjugated GRN163, as demonstrated in hepatoma cell xenografts (FIG. 1) and flank CAG myeloma tumor xenografts (FIG. 2) following i.v. administration.

Administration of GRN163L inhibited tumor growth in mice (A549-luc IV lung metastases model) for at least 4 weeks after i.v. injection of cancer cells. The dosage was 1 μM biweekly for 5 weeks prior to injection of cancer cells, followed by 5 mg/kg twice weekly after injection. Controls showed substantial tumor growth, but none was apparent in the GRN163L-treated mouse.

IV. Combination Therapy with Proteasome and Telomerase Inhibitors

Therapeutic benefits for treatment of cancer can be realized by combining a telomerase inhibitor with other anti-cancer agents. In one embodiment, the telomerase inhibitor is an hTR template blocking agent, as described above. Preferably, the combination provides a enhanced inhibiting effect relative to either component alone. More preferably, the combination of telomerase inhibition with chemotherapeutic treatment has a supraadditive effect; that is, the combined benefit is greater than would be expected simply from the additive effects of the two therapeutic approaches. This is demonstrated herein for the combination of a telomerase inhibitor and the proteasome inhibitor bortezomib (Velcade™).

In accordance with the present invention, it has been discovered that combined exposure of cancer cells to both a proteasome inhibitor of the type effective to inhibit the chymotrypsin activity of proteasomes, and a telomerase inhibitor, enhances the extent to which cell proliferation is inhibited relative to the proteasome inhibitor alone or the telomerase inhibitor alone. The effect is seen both for inhibition of cancer cell growth in vitro, where the inhibition is evidenced by a reduced rate of cell proliferation, and for in vivo treatment of cancer in a mammalian subject, where the inhibition is evidenced by a reduced rate of tumor growth and/or increased survival time of the subject being treated.

A. Combined Therapy In Vivo

In practicing the method of the invention for in vivo treatment, a subject having a cancer type that is responsive to a proteasome inhibitor, or a subject currently receiving cancer therapy with a proteasome inhibitor, is initially identified as a candidate for the combined therapy. Exemplary cancer indications include, for example, multiple myeloma, for which the proteasome inhibitor bortezomib is currently indicated. Recent studies have shown antitumor activity for this drug in breast, non-small cell lung (NSCLC), colon, prostate, neuroendocrine, and renal cancers, as well as in melanoma, sarcoma, chronic myelogenoius leukemia, non-Hodgkin's lymphoma, and mantle cell lymphoma.

Thus, an aspect of the invention involves identifying cancer patients who are candidates for effective anti-cancer treatment with a telomerase inhibitor. The candidate patients are those whose cancer is responding to treatment with bortezomib, or a related proteasome inhibitor, but for whom combined treatment with a telomerase inhibitor is desired to enhance the anti-tumor efficacy of the proteasome inhibitor alone.

The cancer should also be one that is responsive to cancer-cell inhibition by telomerase inhibition. As noted above, oligonucleotide telomerase inhibitors, as exemplified by GRN163 and GRN163L, have shown inhibitory activity in vitro against human kidney, lung, pancreatic, brain, colon, prostate, breast, leukemia, lymphoma, myeloma, epidermal, cervical, ovarian and liver cancer cells, and in vivo, via local and systemic delivery, against human brain, prostate, lymphoma, myeloma, cervical, lung, and liver cancer cells. Other preferred targets include small cell lung, esophageal, head and neck, and stomach cancers.

In the preferred treatment method, the subject is administered the proteasome inhibitor, e.g., bortezomib, in an amount that is effective at inhibiting proliferation of cancer cells in the subject. The dose administered and the dosing schedule will follow, for example, known or recommended doses for the proteasome inhibitor employed, as indicated, for example, in the drug product insert or published clinical or animal-model data. One advantage of the present invention is that lower-than-normal doses of the proteasome inhibitor may be administered, if necessary, due to the compensating enhancement effect of the telomerase inhibitor. Such a protocol allows for a reduced dosage of the proteasome inhibitor, which can have significant toxic effects at higher dosages.

Thus, a kit containing a dose of the telomerase inhibitor could contain a product insert having one set of directions for using the inhibitor in monotherapy, and another set of directions for using the inhibitor in a combination therapy with a proteasome inhibitor, such as bortezomib. The set of instructions for the combination therapy could recommend (i) a lower dose of the telomerase inhibitor, when used in combination with the proteasome inhibitor, (ii) a lower dose of the proteasome inhibitor, when used in combination with the telomerase inhibitor and/or (iii) a different dosing regimen for one of both inhibitors than would normally be recommended.

The telomerase inhibitor may be administered, before, during, or after administration of the proteasome inhibitor. Typically, the two inhibitors are administered in a common dosing regimen, as described below, and the two inhibitors themselves may be administered in a combined-drug composition, or separately, for example, by enteral administration of the proteasome inhibitor and parenteral administration of the telomerase inhibitor. However, a dosing regimen in which the telomerase inhibitor is administered before or after administering the proteasome inhibitor is also contemplated. For example, a person under treatment with a proteasome inhibitor may be subsequently placed on a combined therapy that includes telomerase inhibitor.

Alternatively, the patient may be initially administered the proteasome inhibitor, followed one-to-several days later with the telomerase treatment. In this regimen, the proteasome inhibitor may function, in part, to sensitize the cancer cells to inhibition by a telomerase inhibition, e.g., by synchronizing the cell-division cycle and/or promoting apoptosis in the cells. Preferred dose levels and dosing schedules are considered further below.

Figure 3:
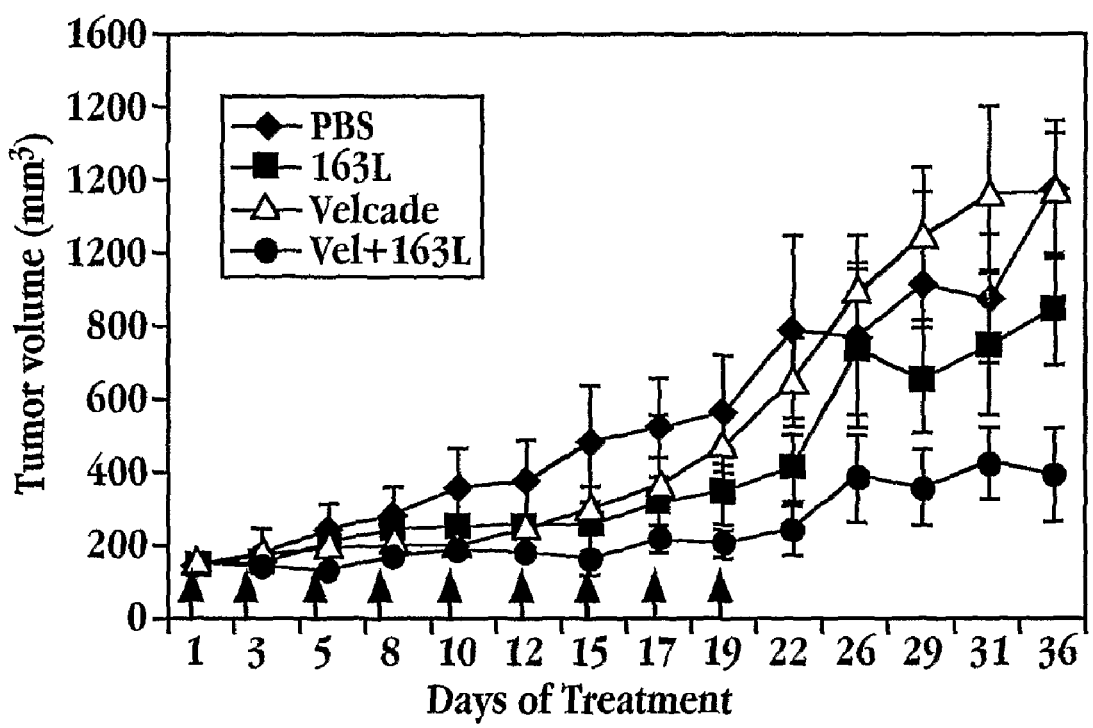
FIG. 3 illustrates a supraadditive effect on inhibition of cancer cells achieved by co-administration of the proteasome inhibitor bortezomib and a telomerase inhibitor, exemplified by administration of bortezomib and the telomerase inhibitor GRN163L, in a multiple myeloma xenograft model (see Section IV.A and Experimental Section D below)

In one exemplary method, the proteasome inhibitor bortezomib is administered in combination with a telomerase-inhibitor oligonucleotide targeted against hTR. FIG. 3, for example, shows the results of the treatment method in which bortezomib is administered in combination with the telomerase inhibitor GRN163L, for the treatment in multiple myeloma in a mouse xenograft model. Details of this study are given in Experimental Section D below. As seen from FIG. 3, treatment with the two inhibitors, over a 36-day treatment period (GRN163 was administered 3 times per week over the treatment period, and bortezomib, at the times indicated by the arrows) limited tumor growth to about 4-fold over the pre-treatment level. With treatment by bortezomib alone, tumor volume increased nearly 12-fold over the same period (close to that of the untreated animal group) and with GRN163L alone, tumor growth increased about 8 fold. Thus, the combined effect of the two inhibitors gave an approximately 300% reduction in tumor size over bortezomib alone, and about a 200% reduction in tumor size over GRN163L alone.

A method similar to that just described was carried out with individual and combined bortezomib and GRN163L therapy in the disseminated CAG multiple myeloma mouse model, as detailed below in Experimental Section E, with the results shown in FIGS. 4A and 4B. In these figures: group 1 represents PBS controls; group 2, GRN163L administered on a WMF schedule; group 3, GRN163L administered on a M-F schedule; group 4, IV administered bortezomib; and groups 5 and 6, combination therapy with bortezomib and GRN163L, summarized in Table 5 below.

Figure 4A:
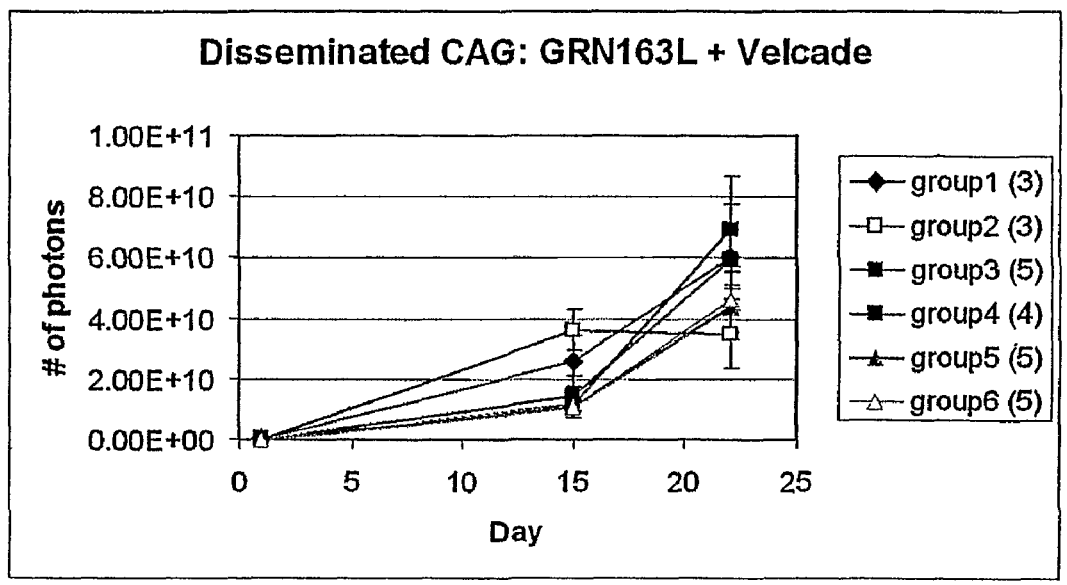
FIGS. 4A and 4B show measurements of tumor size by bioluminescence imaging in a disseminated CAG model, with treatment by bortezomib alone, GRN163L alone, and the two inhibitors together (4A) and the effect of the individual and combined therapies on survival time of mice in the disseminated CAG myeloma model (4B) (see Section IV.A and Experimental Section E below)
Figure 4B:
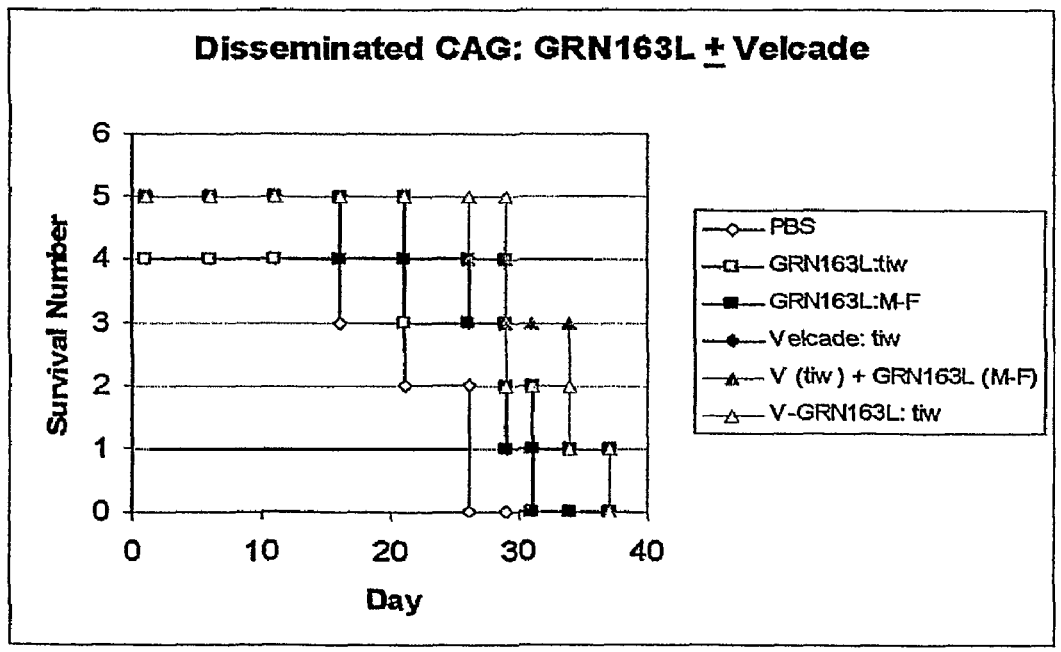

As seen in FIG. 4A, all therapies produced a lower rate of tumor growth, relative to untreated control. A significant increase ($p<0.01$) in survival relative to PBS controls was observed in each group treated with a single agent (Groups 2-4). GRN163L administered on either a WMF schedule (Group 2) or M-F schedule (Group 3) was significantly better than bortezomib (Group 4) alone ($p=0.05$ and $p<0.001$, respectively). Combination chemotherapy significantly increased the survival of mice compared to the PBS and single agent controls (FIG. 4B, Groups 5 and 6).

These experiments also showed that administration of GRN163L at 36 mg/kg alternating with bortezomib was as effective as administration of GRN163L at 36 mg/kg tiw (three times a week) combined with bortezomib (compare Group 5 with Group 6). In other words, in combination with bortezomib, similar survival benefit could be achieved with half the dose of GRN163L.

TABLE 5

Description of groups in disseminated CAG model

| | M | W | F | M | W | F |
|---|---|---|---|---|---|---|
| Group 1 | — | — | — | — | — | — |
| Group 2 | — | G | — | G | — | G |
| Group 3 | G | G | G | G | G | G |
| Group 4 | Vel | — | Vel | — | Vel | — |
| Group 5 | Vel +G | G | Vel +G | G | Vel +G | G |
| Group 6 | Vel | G | Vel | G | Vel | G |

Figure 5A:
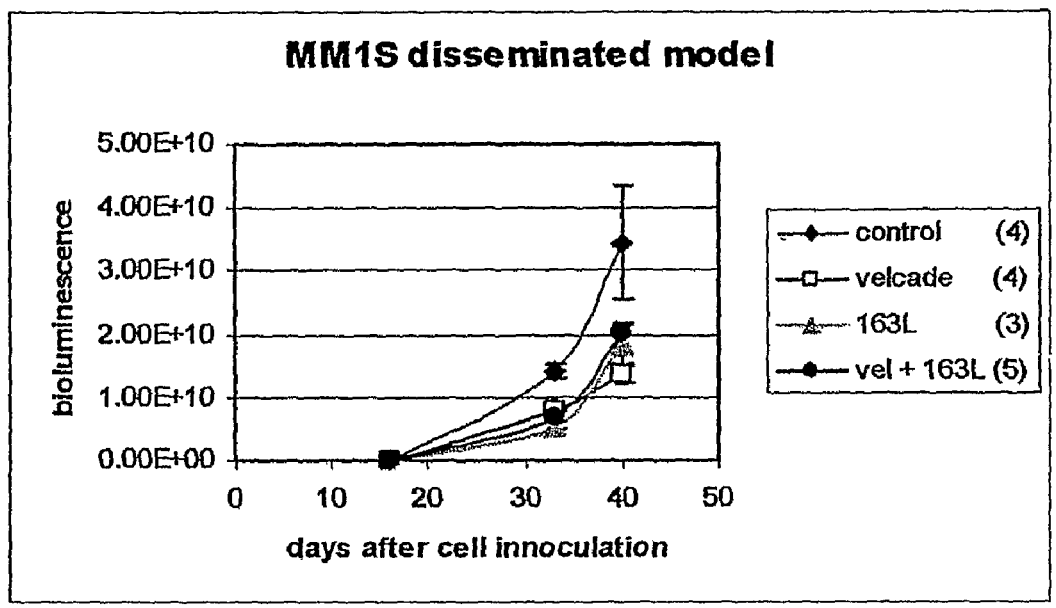
FIGS. 5A and 5B show measurements of tumor size by bioluminescence imaging in a disseminated MM1s model, with treatment by bortezomib alone, GRN163L alone, and the two inhibitors together (5A) and the effect of the individual and combined therapies on survival time of mice in the disseminated MM1s myeloma model (5B) (see Section IV.A and Experimental Section F below).

In another method, the combined therapy was applied to animals in the an animal model having a xenograft of MM1s multiple myeloma cells, as detailed in Experimental Section F below. Briefly, GRN163L was administered by intraperitoneal (ip) injection three time a week at 36 mg/kg for 4 weeks alone or in combination with 6 doses of bortezomib (0.25 mg/kg). Tumor mass, as measured by bioluminescence from the tumors, was significantly reduced for both individual and combined treatment, as seen in FIG. 5A. Similarly, highest rates of survival were seen with bortezomib alone and with the combined therapy.

B. Administration

The therapeutic protocol for administering such combinations will depend on various factors including, but not limited to, the type of cancer, the age and general health of the patient, the aggressiveness of disease progression, the TRF length (terminal restriction fragment length; see Section V below) and telomerase activity of the diseased cells to be treated, and the ability of the patient to tolerate the agents that comprise the combination.

In general, treatment of all carcinoma and hematological malignancy types is contemplated. In selected embodiments, the target disease comprises a solid tumor; in other embodiments, the target disease comprises a hematological malignancy. An exemplary course of treatment involves multiple doses. Sequence of combination treatments will be determined by clinical compliance criteria and/or preclinical or clinical data supporting dose optimization strategies to augment efficacy or reduce toxicity of the combination treatment. In general, various combinations of the telomerase inhibitor and proteasome inhibitor may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. The time between dosages may be for a period from about 1-6 hours, to about 6-12 hours, to about 12-24 hours, to about 1-2 days, to about 1-2 wk or longer following the initiation of treatment. During a course of treatment, the need to complete the planned dosings may be re-evaluated.

The compounds may be administered by direct injection of a tumor or its vasculature. Alternatively, the tumor may be infused or perfused with the therapeutic compounds using any suitable delivery vehicle. The compounds may be administered locally to an affected organ. Systemic administration may also be performed. Continuous administration may be applied where appropriate; for example, where a tumor is excised and the tumor bed is treated to eliminate residual disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The therapeutic agents are administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

The amount of each agent per dose and the number of doses required to achieve such effects will vary depending on many factors including the disease indication, characteristics of the patient being treated and the mode of administration. Typically, the formulation and route of administration will provide a local concentration at the disease site of between 1 nM and 100 μM of each agent. The physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy. In general, the compounds are administered at a concentration that affords effective results without causing excessive harmful or deleterious side effects.

In accordance with the invention, the amount of the agent used in combination with a telomerase inhibitor, especially with respect to a chemotherapeutic agent such as bortezomib, may be less than would be required for the agent used in non-combination therapy.

C. Formulations

The pharmaceutical carrier(s) employed may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration, the carrier can also be an oily ester such as ethyl oleate and isopropyl myristate. Sterile carriers are useful in sterile liquid form compositions for parenteral administration. Sterile liquid pharmaceutical compositions, solutions or suspensions can be utilized by, for example, intraperitoneal injection, subcutaneous injection, intravenously, or topically. The compositions can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the compositions may be formulated into an aqueous or partially aqueous solution, which can then be utilized in the form of an aerosol.

The compositions may be administered topically as a solution, cream, or lotion, by formulation with pharmaceutically acceptable vehicles containing the active compound. The compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Modes of administration and formulation may be dependent on the drug and its approved mode of administration. For example, when the chemotherapeutic agent is bortezomib, i.v. administration is indicated. When the telomerase inhibitor is GRN163L, formulation in 0.9% sodium chloride (normal saline) and administration by i.v. is a preferred route, preferably via infusion over 4-8 hours, e.g. a 6 hr infusion. While the lipid-conjugated oligonucleotides described herein, such as GRN163L, have superior characteristics for cellular and tissue penetration, these and other compounds may be formulated to provide further benefit in this area, e.g. in liposome carriers. The use of liposomes to facilitate cellular uptake is described, for example, in U.S. Pat. Nos. 4,897,355 and 4,394,448, and numerous publications describe the formulation and preparation of liposomes. Liposomal formulations can also be engineered, by attachment of targeting ligands to the liposomal surface, to target sites of neovascularization, such as tumor angiogenic regions. The compounds can also be formulated with additional penetration/transport enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Other useful adjuvants include substrates for transendothelial migration, such as glucose uptake systems for facilitated egress from the vascular space to the tumor microenvironment.

V. Measurement of Telomere Length, Telomerase Activity, and/or Cell Proliferation When employing a therapeutic regimen that involves administration of a telomerase inhibitor, it may be useful to determine telomere length and/or telomerase activity in a cell or tissue sample. These parameters can be measured by assays known in the art. Telomere length can be measured by a flow cytometry method using fluorescence in situ hybridization, referred to as flow FISH (see e.g. M. Hultdin et al., *Nucleic Acids Res.* 26(16):3651-6, 1998; N. Rufer et al., *Nature Biotechnology* 16:743-7, 1998). Other methods include terminal restriction fragment (TRF) analysis, in which genomic DNA is digested with a restriction enzyme having a four-base recognition sequence not present in telomere repeat sequences, and the restriction fragments are separated according to size, e.g. by gel electrophoresis. See, for example, U.S. Pat. No. 5,489,508 (West et al.) and Harley et al., *Nature* 345:458, 1990. The West et al. patent also describes methods of measuring telomere length by a "anchored terminal primer" method and by a modified Maxam-Gilbert reaction.

In addition, a more rapid response to a telomerase inhibiting agent may be predicted for tumor cells having shorter telomeric DNA, although telomerase has been shown to have other inhibitory effects independent of telomere length. (e.g. Stewart et al., *PNAS* 99:12606, 2002; Zhu et al., *PNAS* 93:6091, 1996; Rubaiyat et al., *Oncogene* 24(8):1320, 2005); and Folini et al., *Curr. Pharm. Design* 11 (9):1105, 2005).

The TRAP assay (see Experimental, below) is a standard method for measuring telomerase activity in a cell extract system (Kim et al., *Science* 266:2011, 1997; Weinrich et al., *Nature Genetics* 17:498, 1997). Briefly, this assay measures the amount of nucleotides incorporated into elongation products (polynucleotides) formed by nucleotide addition to a labeled telomerase substrate or primer. The TRAP assay is described in detail in U.S. Pat. Nos. 5,629,154, 5,837,453 and 5,863,726, and its use in testing the activity of telomerase inhibitory compounds is described in various publications, including WO 01/18015. In addition, the following kits are available commercially for research purposes for measuring telomerase activity: TRAPeze™ XK Telomerase Detection Kit (Intergen Co., Purchase N.Y.); and TeloTAGGG Telomerase PCR ELISA plus (Roche Diagnostics, Indianapolis Ind.).

The anticancer activity of the therapeutic combinations can be evaluated using standard in vitro and in vivo assays. The ability of a composition to specifically inhibit the growth of tumor cells can be assayed using tumor cell lines in vitro, or in xenograft animal models in vivo. A preferred protocol for such growth curve assays is the short term cell viability assay described in Asai et al. (2003, cited above). In established xenograft models of human tumors, the test compound is administered either directly to the tumor site or systemically, and the growth of the tumor is followed by physical measurement. A preferred example of a suitable in vivo tumor xenograft assay is also described in Asai et al. (2003, cited above). Other examples are described in Scorski et al., *Proc. Natl. Acad. Sci. USA,* 94: 3966-3971 (1997) and Damm et al., *EMBO J.,* 20:6958-6968 (2001).

EXPERIMENTAL

A. Preparation and Lipid Conjugation of Oligonucleotide N3'→P5'Phosphoramidates or N3'→P5' Thiophosphoramidates These compounds may be prepared as described, for example, in McCurdy et al., *Tetrahedron Letters* 38:207-210 (1997) or Pongracz & Gryaznov, *Tetrahedron Letters* 49:7661-7664 (1999). The starting 3'-amino nucleoside monomers may be prepared as described in Nelson et al., *J. Org. Chem.* 62:7278-7287 (1997) or by the methods described in Gryaznov et al., US Appn. Pubn. No. 2006/0009636.

A variety of synthetic approaches can be used to conjugate a lipid moiety L to the oligonucleotide, depending on the nature of the linkage selected; see, for example, Mishra et al., *Biochim. et Biophys. Acta* 1264:229-237 (1995), Shea et al., *Nucleic Acids Res.* 18:3777-3783 (1995), or Rump et al., *Bioconj. Chem.* 9:341-349 (1995). Typically, conjugation is achieved through the use of a suitable functional groups at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al, *Bioorg. Med. Chem.* 9:1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Appn. Pubn. No. 2005/0113325, which is incorporated herein by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino group of the fully protected support-bound oligonucleotide may also be reacted with a suitable lipid aldehyde, followed by reduction with sodium cyanoborohydride, which produces an amine linkage.

For attachment of a lipid to the 5' terminus, as also described in US Appn. Pubn. No. 2005/0113325, the oligonucleotide can be synthesized using a modified, lipid-containing solid support. Reaction of 3-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S—represents a long chain alkyl amine CPG support, and R represents a lipid.

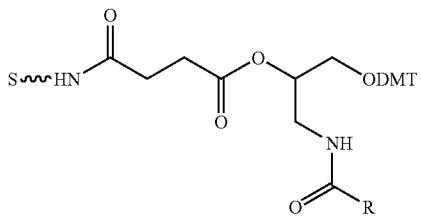

This procedure is followed by synthesis of the oligonucleotide in the 5' to 3' direction, as described, for example, in Pongracz & Gryaznov (1999), starting with deprotection and phosphitylation of the -ODMT group. This is effective to produce, for example, the following structure, after cleavage from the solid support:

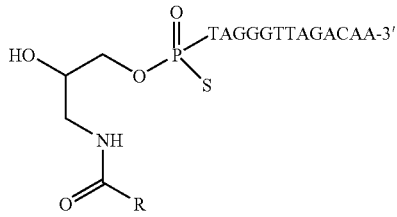

The structure above, when —R is —(CH$_2$)$_{14}$CH$_3$ (palmitoyl), is designated herein as GRN163L.

B. FlashPlate™ Assay

This assay was carried out essentially as described in Asai et al., Cancer Research, 63:3931 3939 (2003). Briefly, the assay detects and/or measures telomerase activity by measuring the addition of TTAGGG telomeric repeats to a biotinylated telomerase substrate primer. The biotinylated products are captured on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

C. TRAP Assay

The ability of a compound to increase or inhibit telomerase activity in a cell can be determined using the TRAP (Telomeric Repeat Amplification Protocol) assay, which is described, for example, in Kim et al., U.S. Pat. No. 5,629,154; Harley et al., U.S. Pat. No. 5,891,639; and Harley et al., PCT Pubn. No. WO 2005/000245. Briefly, telomerase-expressing tumor cell lines are incubated with test compositions, lysed, and treated with a labeled oligonucleotide telomerase substrate, appropriate primers, and internal standard for quantitation purposes. Depending on the telomerase activity of the medium, telomere repeats will be added to the substrate, to form telomerase extended products. The mixture is incubated at room temperature, followed by multiple cycles of PCR. The mixture is separated on a gel, and labeled extension product is detected and quantitated via comparison with the internal standard.

D. In Vivo Antitumor Assay Employing GRN163L in Combination with Bortezomib

CAG/HSV-TK/GFP/Luc cells (approx. 10$^7$; TRF length 2.7 Kb) were implanted subcutaneously into NOD/SCID mice one day after irradiation. Treatment was initiated when tumors reached ~100 mm$^3$. Groups of four mice each were treated in accordance with one of three protocols: (1) GRN163L alone, three times per week (tiw) at 36 mg/kg for four weeks; (2) bortezomib alone, tiw at 0.125 μg per mouse for three weeks (9 doses); and (3) these treatments in combination (see FIG. 3). The days when bortezomib was administered are indicated with arrows in FIG. 3. A fourth group received saline buffer alone as a control.

As shown in the Figure, this dose of bortezomib was minimally effective alone (protocol 2), and this dose of GRN163L alone (protocol 1) reduced tumor mass by about 30%. In combination (protocol 3), these agents reduced tumor mass by about 68%. No significant weight loss was observed.

E. The Effect of Combined Therapy in a Disseminated CAG Model

The effect of GRN163L in combination with bortezomib was tested in a disseminated CAG model. The CAG MM cell line (telomere length 2.7 Kb) was transfected with a retroviral vector encoding a triple fusion gene for HSV-TK, firefly luciferase and green fluorescence protein, and whole animal bioluminescence imaging was undertaken in a disseminated NOD/SCID model with extensive spinal cord and bone marrow tumor infiltration. NOD/SCID mice were not irradiated with gamma ray before cell implantation. GRN163L or PBS was administered by intraperitoneal (i.p.) injections at 36 mg/kg for 5 weeks (Table 1). Bortezomib was administered intravenously at a dose of 0.25 mg/kg (Table 1).

In these experimental settings, bortezomib was used to target the tumor mass and to help to increase the survival time of the mice so that GRN163L could be effective on more primitive cancer cells that would escape the toxic effects of non-specific chemotherapy in long term. The results are discussed in Section IVA above, with reference to FIGS. 4A-B.

F. The Effect of Combined Therapy in a Disseminated MM1s Model

Figure 5B:
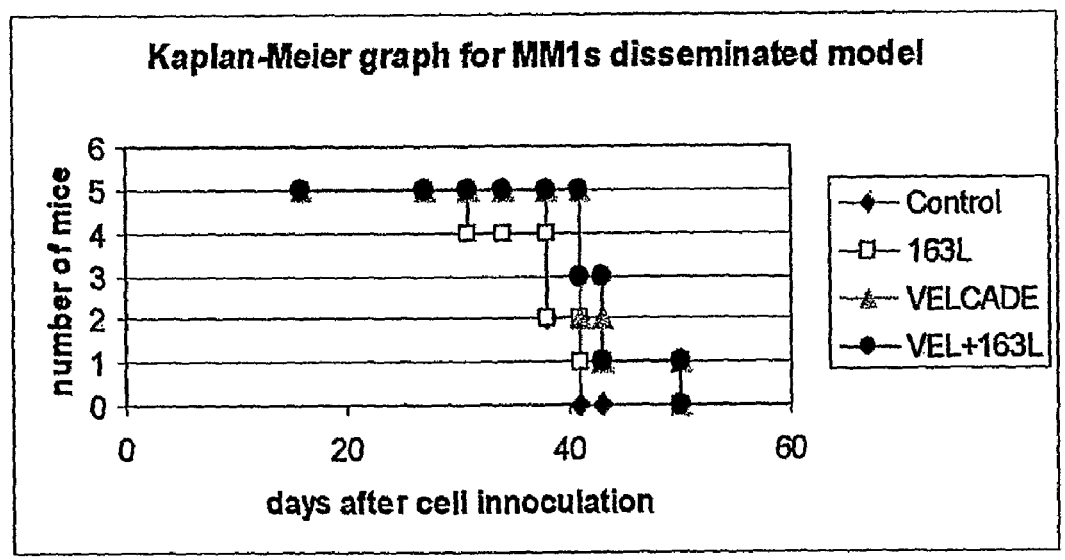

MM1s MM cell line with a short average telomere length (2.5 Kb) was used in a xenograft model to test the effect of GRN163L on tumor growth in vivo. The MM1s cells were transfected with a retroviral vector encoding a double fusion gene for firefly luciferase and green fluorescence protein, and whole animal bioluminescence imaging was undertaken in a disseminated NOD/SCID model with extensive spinal cord and bone marrow tumor infiltration. NOD/SCID mice were irradiated with 300 rads of gamma ray before cell implantation. GRN163L was administered by intraperitoneal (i.p.) injections three times in two weeks at 36 mg/kg for 4 weeks alone or in combination with 6 doses of bortezomib (0.25 mg/kg). The results are discussed in Section IVA above, with reference to FIGS. 5A-B.

Although the invention has been described with respect to particular embodiments and applications, those skilled in the art will appreciate the range of applications and methods of the invention disclosed herein.

SEQUENCE LISTING

SEQ ID NO: 1: the RNA component of human telomerase (hTR):

```
GGGUUGCGGA GGGUGGGCCU GGGAGGGGUG GUGGCCAUUU UUUGUCUAAC CCUAACUGAG   60
AAGGGCGUAG GCGCCGUGCU UUUGCUCCCC GCGCGCUGUU UUUCUCGCUG ACUUUCAGCG  120
GGCGGAAAAG CCUCGGCCUG CCGCCUUCCA CCGUUCAUUC UAGAGCAAAC AAAAAAUGUC  180
AGCUGCUGGC CCGUUCGCCU CCCGGGGACC UGCGGCGGGU CGCCUGCCCA GCCCCCGAAC  240
CCCGCCUGGA GCCGCGGUCG GCCCGGGGCU UCUCCGGAGG CACCCACUGC CACCGCGAAG  300
AGUUGGGCUC UGUCAGCCGC GGGUCUCUCG GGGGCGAGGG CGAGGUUCAC CGUUUCAGGC  360
CGCAGGAAGA GGAACGGAGC GAGUCCCGCC GCGGCGCGAU UCCCUGAGCU GUGGGACGUG  420
CACCCAGGAC UCGGCUCACA CAUGCAGUUC GCUUUCCUGU UGGUGGGGGG AACGCCGAUC  480
GUGCGCAUCC GUCACCCCUC GCCGGCAGUG GGGGCUUGUG AACCCCCAAA CCUGACUGAC  540
UGGGCCAGUG UGCU
```

SEQ ID NOS: 2-26, nucleotide sequences of targeting agents against SEQ ID NO: 1

| Sequence | SEQ ID |
|---|---|
| ACATTTTTTGTTTGCTCTAG | 2 |
| GCTCTAGAATGAACGGTGGAAGGCGGCAGG | 3 |
| GTGGAGGCGGCAGG | 4 |
| GGAAGGCGGCAGG | 5 |
| GTGGAAGGCGGCA | 6 |
| GTGGAAGGCGG | 7 |
| CGGTGGAAGGCGG | 8 |
| ACGGTGGAAGGCG | 9 |
| AACGGTGGAAGGCGGC | 10 |
| ATGAACGGTGGAAGGCGG | 11 |
| TAGGGTTAGACAA | 12 |
| CAGTTAGGGTTAG | 13 |
| TAGGGTTAGACA | 14 |
| TAGGGTTAGAC | 15 |
| GTTAGGGTTAG | 16 |
| GTTAGGGTTAGAC | 17 |
| GTTAGGGTTAGACAA | 18 |
| GGGTTAGAC | 19 |
| CAGTTAGGG | 20 |
| CCCTTCTCAGTT | 21 |
| CGCCCTTCTCAG | 22 |
| TAGGTGTAAGCAA | 23 |
| TTGTCTAACCCTA | 24 |
| GTTGAGTGTAG | 25 |
| TTAGGG | 26 |
| TTTTTTTTTT | 27 |

The invention claimed is:

1. A method for inhibiting the proliferation of multiple myeloma cancer cells, the method comprising
   (a) exposing the cells to the proteasome inhibitor bortezomib, and
   (b) either proceeding, following, or concomitantly with step (a), exposing the cells to a telomerase inhibitor, wherein the telomerase inhibitor includes an oligonucleotide which is characterized by:
      (i) N3'→P5' thiophosphoramidate internucleoside linkages;
      (ii) having the sequence identified as SEQ ID NO: 12; and
      (iii) a palmitoyl (C16) moiety linked to the 5' terminus of the oligonucleotide via a glycerol or aminoglycerol linker;
   wherein said method provides a supraadditive inhibiting effect relative to the inhibiting effects of the individual agents.

2. The method of claim 1, wherein the oligonucleotide is 10-20 bases in length.

3. The method of claim 1, wherein the telomerase inhibitor is the compound designated herein as GRN163L.

4. The method of claim 1, for use in treating a subject diagnosed with multiple myeloma, wherein exposing step (a) includes administering the proteasome inhibitor to the subject in an amount effective, when the inhibitor is administered alone, to inhibit proliferation of multiple myeloma cancer cells in the subject.

5. The method of claim 4, wherein each exposing step (a) and (b) includes administering the respective inhibitor to the subject in an amount effective, when each inhibitor is administered alone, to inhibit proliferation of multiple myeloma cancer cells in the subject.

6. The method of claim 4, wherein the telomerase inhibitor is the compound GRN163L, and step (b) includes infusing the telomerase inhibitor intravenously into the subject, under infusion conditions effective to produce a blood concentration of the telomerase inhibitor of between 1 nM and 100 μM.

7. The method of claim 1, wherein the amount of each inhibitor to which the cells are exposed is effective, by itself, to inhibit proliferation of the cancer cells.

8. A method for enhancing the anti-cancer treatment efficacy of the proteasome inhibitor bortezomib in a subject diagnosed with multiple myeloma, the method comprising administering to the subject, before, during, or after administering the proteasome inhibitor, an oligonucleotide telomerase inhibitor which comprises an oligonucleotide which is characterized by:
   (i) N3'→P5' thiophosphoramidate internucleoside linkages;
   (ii) having the sequence identified as SEQ ID NO: 12; and
   (iii) a palmitoyl (C16) moiety linked to the 5' terminus of the oligonucleotide via a glycerol or aminoglycerol linker;
   wherein said method provides a supraadditive anti-cancer effect relative to the anti-cancer effects of the individual agents.

9. The method of claim 8, wherein the telomerase inhibitor is administered in an amount effective to inhibit the proliferation of multiple myeloma cancer cells in the subject, when the telomerase inhibitor is administered alone.

10. The method of claim 8, wherein enhanced treatment efficacy is evidenced by an increased survival time of the subject, inhibition of tumor growth in the subject, or a combination thereof.

11. The method of claim 8, wherein the oligonucleotide telomerase inhibitor is GRN163L.

12. The method of claim 11, wherein said administering includes infusing the oligonucleotide telomerase inhibitor intravenously into the subject, under infusion conditions effective to produce a blood concentration of the inhibitor of between 1 nM and 100 μM.

13. The method of claim 8, wherein the two inhibitors are administered to the subject as a composition containing both inhibitors.

14. A kit for use in cancer therapy, the kit comprising
   (a) a dose of the proteasome inhibitor bortezomib, in an amount of the inhibitor effective, when administered alone, to inhibit the proliferation of cancer cells in the subject, and
   (b) a dose of an oligonucleotide telomerase inhibitor is characterized by:
      (i) N3'→P5' thiophosphoramidate internucleoside linkages;
      (ii) having the sequence identified as SEQ ID NO: 12; and
      (iii) a palmitoyl (C16) moiety linked to the 5' terminus of the oligonucleotide via a glycerol or aminoglycerol linker;
   wherein a combination of the proteasome inhibitor and telomerase inhibitor provides a supraadditive inhibiting effect on the proliferation of cancer cells relative to the inhibiting effects of the individual agents.

15. The kit of claim 14, wherein the telomerase inhibitor is the compound designated herein as GRN163L.

16. The kit of claim 14, wherein the dose of the oligonucleotide telomerase inhibitor is an amount effective, when administered alone, to inhibit proliferation of cancer cells in the subject.

* * * * *

SEQUENCE LISTING

<160> NUMBER OF SEQ ID NOS: 27

<210> SEQ ID NO 1
<211> LENGTH: 554
<212> TYPE: RNA
<213> ORGANISM: Homo sapiens

<400> SEQUENCE: 1

```
gqguugcgga ggguqqgccu gggaggggug guggccauuu uuugucuaac ccaacugag    60
aagggcguag gcgccgugcu uuugcucccc gcgcgcuguu uuucucgcug acuuucagcg  120
ggcggaaaag ccucggccug ccgccuucca ccguucauuc uagagcaaac aaaaaauguc  180
agcugcuggc ccguucgccu cccggggacc ugcggcgggu cgccugccca gcccccgaac  240
```

```
cccgccugga gccgcggucg gcccggggcu ucuccggagg cacccacugc caccgcgaag    300
aguugggcuc ugucagccgc gggucucucg ggggcgaggg cgagguucac cguuucaggc    360
cgcaggaaga ggaacggagc gaguccogcc gcggcgcgau ucccugagcu gugggacgug    420
cacccaggac ucggcucaca caugcaguuc gcuuccugu ugguggggg aacgccgauc     480 gugcgcaucc gucaccccuc gccggcagug ggggcuugug aaccccccaaa ccugacugac    540 ugggccagug ugcu                                                      554
```

```
<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2 acatttttg tttgctctag                                                20

<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
gctctagaat gaacggtgga aggcggcagg                                     30

<210> SEQ ID NO 4
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 4
gtggaggcgg cagg                                                      14

<210> SEQ ID NO 5
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 5
ggaaggcggc agg                                                       13

<210> SEQ ID NO 6
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 6
gtggaaggcg gca                                                       13

<210> SEQ ID NO 7
<211> LENGTH: 11
<212> TYPE: DNA
<213> ORGANISM: Artificial Sequence
<220> FEATURE:
<223> OTHER INFORMATION: Synthetic Oligonucleotide
```

```
<400> SEQUENCE: 7
gtggaaggcg g                                                           11

<210> SEQ ID NO 8
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 8
cggtggaagg cgg                                                         13

<210> SEQ ID NO 9
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 9
acggtggaag gcg                                                         13

<210> SEQ ID NO 10
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 10
aacggtggaa ggcggc                                                      16

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
atgaacggtg gaaggcgg                                                    18

<210> SEQ ID NO 12
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 12
tagggttaga caa                                                         13

<210> SEQ ID NO 13
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 13
cagttagggt tag                                                         13

<210> SEQ ID NO 14
<211> LENGTH: 12
```

```
<212> TYPE: DNA
<213> ORGANISM: Artificial Sequence
<220> FEATURE:
<223> OTHER INFORMATION: Synthetic Oligonucleotide

<400> SEQUENCE: 14
tagggttaga ca                                                          12

<210> SEQ ID NO 15
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 15
tagggttaga c                                                           11

<210> SEQ ID NO 16
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 16
gttagggtta g                                                           11

<210> SEQ ID NO 17
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 17
gttagggtta gac                                                         13

<210> SEQ ID NO 18
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 18
gttagggtta gacaa                                                       15

<210> SEQ ID NO 19
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 19 gggttagac                                                               9

<210> SEQ ID NO 20
<211> LENGTH: 9
<212> TYPE: DNA
<213> ORGANISM: Artificial Sequence
<220> FEATURE:
<223> OTHER INFORMATION: Synthetic Oligonucleotide

<400> SEQUENCE: 20 cagttaggg                                                               9
```

```
<210> SEQ ID NO 21
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 21
cccttctcag tt                                                             12

<210> SEQ ID NO 22
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 22
cgcccttctc ag                                                             12

<210> SEQ ID NO 23
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 23
taggtgtaag caa                                                            13

<210> SEQ ID NO 24
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 24
ttgtctaacc cta                                                            13

<210> SEQ ID NO 25
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 25
gttgagtgta g                                                              11

<210> SEQ ID NO 26
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 26 ttaggg                                                                     6

<210> SEQ ID NO 27
<211> LENGTH: 10
```

```
<212> TYPE: DNA
<213> ORGANISM: Artificial Sequence
<220> FEATURE:
<223> OTHER INFORMATION: Synthetic Oligonucleotide

<400> SEQUENCE: 27
tttttttttt                                                                10
```